(12) United States Patent
Kim et al.

(10) Patent No.: US 8,030,315 B2
(45) Date of Patent: Oct. 4, 2011

(54) DPP-IV INHIBITOR INCLUDING BETA-AMINO GROUP, PREPARATION METHOD THEREOF AND PHARMACEUTICAL COMPOSITION CONTAINING THE SAME FOR PREVENTING AND TREATING DIABETES OR OBESITY

(75) Inventors: Heung Jae Kim, Seongnam-si (KR); Woo Young Kwak, Yongin-si (KR); Chang Yell Shin, Seoul (KR); Hadong Kim, Suwon-si (KR); Jong Pil Min, Yongin-si (KR); Kyung Jin Park, Seoul (KR); Jae Young Lee, Yongin-si (KR); Song-Hyen Choi, Suwon-si (KR); Tae Hyun Yoon, Seoul (KR); Hae-Sun Kim, Seoul (KR); Ji Myun Jang, Yongin-si (KR); Mi-Kyung Kim, Suwon-si (KR); Moon-Ho Son, Suwon-si (KR); Soon Hoe Kim, Suwon-si (KR); Moohi Yoo, Seoul (KR)

(73) Assignee: Dong-A Pharm. Co., Ltd., Seoul (KR)

( * ) Notice: Subject to any disclaimer, the term of this patent is extended or adjusted under 35 U.S.C. 154(b) by 0 days.

(21) Appl. No.: 12/596,281

(22) PCT Filed: Apr. 18, 2008

(86) PCT No.: PCT/KR2008/002203
§ 371 (c)(1),
(2), (4) Date: Oct. 16, 2009

(87) PCT Pub. No.: WO2008/130151
PCT Pub. Date: Oct. 30, 2008

(65) Prior Publication Data
US 2010/0120790 A1    May 13, 2010

(30) Foreign Application Priority Data

Apr. 19, 2007 (KR) .................. 10-2007-0038462

(51) Int. Cl.
*A61K 31/4965* (2006.01)
*C07D 241/04* (2006.01)

(52) U.S. Cl. .................... 514/255.01; 544/384
(58) Field of Classification Search .......... 514/255.01; 544/384
See application file for complete search history.

(56) References Cited

FOREIGN PATENT DOCUMENTS

| WO | 2004/037169 A2 | 5/2004 |
| WO | 2005/011581 A2 | 2/2005 |
| WO | 2005/056003 A1 | 6/2005 |
| WO | 2005/056541 A1 | 6/2005 |
| WO | 2005/095343 A1 | 10/2005 |
| WO | 2005/121131 A1 | 12/2005 |
| WO | 2005/123685 A1 | 12/2005 |
| WO | WO 2005/123685 | * 12/2005 |
| WO | 2006/104997 A2 | 10/2006 |

OTHER PUBLICATIONS

Biftu, et al., (3R)-4-[(3R)-3-Amino-4-(2,4,5-trifluorophenyl)butanoyl]-3-(2,2,2- trifluoroethyl)-1,4-diazepan-2-one, a selective dipeptidyl peptidase IV inhibitor for the treatment of type 2 diabetes, Bioorganic & Medicinal Chemistry Letters, 2007, 17:49-52.

Coumar, et al., 3-[2-((2S)-2-Cyano-pyrrolidin-1-yl)-2-oxo-ethylamino]-3-methyl-butyramide analogues as selective DPP-IV inhibitors for the treatment of type-II diabetes, Bioorganic & Medicinal Chemistry Letters, 2007, 17:1274-1279.

* cited by examiner

*Primary Examiner* — Andrew D Kosar
*Assistant Examiner* — Erich A Leeser
(74) *Attorney, Agent, or Firm* — Lucas & Mercanti, LLP (57) ABSTRACT

The present invention provides a novel heterocyclic compound containing a beta-amino group, a method for preparing the same, and a pharmaceutical composition comprising the same heterocyclic compound or a pharmaceutically acceptable salt thereof as an active ingredient. The heterocyclic compound of the present invention exhibits excellent DPP-IV inhibitory activity and bioavailability and therefore can be useful for the prophylaxis or treatment of DPP-IV-related diseases such as diabetes or obesity.

13 Claims, 2 Drawing Sheets

DPP-IV INHIBITOR INCLUDING BETA-AMINO GROUP, PREPARATION METHOD THEREOF AND PHARMACEUTICAL COMPOSITION CONTAINING THE SAME FOR PREVENTING AND TREATING DIABETES OR OBESITY

CROSS-REFERENCE TO RELATED APPLICATIONS

This application is a 371 of PCT/KR2008/002203 filed on Apr. 18, 2008, which claims the benefit of Korean Patent Application No. 10-2007-0038462 filed on Apr. 19, 2007, the contents of each of which are incorporated herein by reference.

TECHNICAL FIELD

The present invention relates to a heterocyclic compound containing a beta-amino group, which has excellent inhibitory activity on dipeptidyl peptidase-IV (hereinafter, referred to as "DPP-IV") and high bioavailability, and a pharmaceutical composition comprising the same heterocyclic compound or a pharmaceutically acceptable salt thereof as an active ingredient.

BACKGROUND ART

The enzyme dipeptidyl peptidase IV, herein abbreviated DPP-IV (and elsewhere as DP-IV, DP-4 or DAP-IV) and also known by the classification EC. 3. 4. 14. 5, is a serine protease (Barrett A. J. et al., Arch. Biochem. Biophys., 1995, 247-250), which cleaves the N-terminal dipeptide from peptides that begin with the sequence H-Xaa-Pro-Y or H-Xaa-Ala-Y wherein Xaa represents any lipophilic amino acid, Pro represents proline, and Ala represents alanine (Heins J., et al., Biochim. et Biophys. Acta 1988, 161). DPP-IV is widely distributed and found in a variety of mammalian tissues such as kidney, liver and small intestine (Hegen M. et al., J. Immunol., 1990, 2908-2914). DPP-IV was first identified as a membrane-bound protein. More recently a soluble form has been identified (Duke-Cohan J. S. et al., J. Biol. Chem., 1995, 14107-14114). According to the recently published study and report, it was revealed that such a soluble form of DPP-IV has the same structure and function as a membrane-bound form of the enzyme and is found without a certain membrane-bound domain in blood (Christine D. et. al, Eur. J. Biochem., 2000, 5608-5613).

Initial interest in DPP-IV has focused on its role in the activation of T lymphocytes. DPP-IV responsible for the activation of T lymphocytes was specifically designated CD26. With the report showing that CD26 binds to or interacts with human immunodeficiency virus (HIV) (Guteil W. G. et al., Proc. Natl. Acad. Sci., 1994, 6594-6598), it was proposed that DPP-IV inhibitors could be useful in the treatment of AIDS (Doreen M. A. et al., Bioorg. Med. Chem. Lett., 1996, 2745-2748).

In addition to a critical role participating in the immune system, the main function of DPP-IV stems from its peptidolytic activity as described above. Attention was particularly given to the role of DPP-IV as it is found that DPP-IV is a key enzyme implicated in the degradation of glucagon-like protein-1 (hereinafter, referred to as "GLP-1") in the small intestine (Mentlein R. et al., Eur. J. Biochem., 1993, 829-835). GLP-1 is the 30 amino-acid peptide hormone which is secreted by intestinal L cells as a response to food intake of the small intestine (Goke R. et. al, J. Biol. Chem., 1993, 19650-19655). Since GLP-1 is known to have potentiating effects on the action of insulin in the control of postprandial blood glucose levels (Hoist J. J. et al., Diabetes Care, 1996, 580-586), it was postulated that DPP-IV inhibitors might also be usefully employed in the treatment of type 2 diabetes. Based on this assumption, an early form of the DPP-IV inhibitor was developed with some reports demonstrating the therapeutic effectiveness of a medicine in animal experiments (Pauly R. P. et al., Metabolism, 1999, 385-389). Further, DPP-IV-deficient mice or rats maintained GLP-1 activity and high insulin levels, resulting in decreased blood glucose levels and such a genetic disruption or mutation of the DPP-IV gene exhibited no significant effect on the survival of individual animals (Marguet D. et al., Proc. Natl. Acad. Sci., 2000, 6874-6879). As a consequence, it was proposed that DPP-IV is feasible as a potent therapeutic agent for the treatment of type 2 diabetes, which resulted in accelerated research and development of the DPP-IV inhibitor.

Binding of GLP-1 with a receptor in a variety of tissues results in satiety (feelings of fullness), delayed gastric emptying, and facilitated growth of pancreatic beta-cells. Therefore, clinical trials for the treatment of type 2 diabetes are gradually increasing through intravenous administration of GLP-1 per se (Verdich C. et al., J. Clin. Endocrinol. Metab., 2001, 4382-4389). An in vivo half-life of GLP-1 is merely 2 min (Kieffer T. J., et al., Endocrinology, 1995, 3585-3596), so such a short half-life is a major obstacle to direct use of GLP-1 as a therapeutic agent. Since then, numerous research groups and institutions have made many attempts toward derivatization of GLP-1, resulting in development and commercialization of a peptide which is capable of protracting the short in vivo half-life (Deacon C. F., Diabetes, 2004, 2181-2189). However, such a GLP-1 derivative still suffers from a fundamental limitation in that it is an injectable formulation. Further, a great deal of interest has been increasingly focused on development of an efficient DPP-IV inhibitor, due to the fact that active GLP-1 (7-36) is degraded by DPP-IV and then converted into inactive GLP-1(9-36) only within a short period of time, e.g. 2 min.

The beginning in the development of DPP-IV inhibitors was similar to the development trend of other inhibitors. That is, most of the research results were for substrate analogues. A representative one of these substrate analogues is a dipeptide derivative which was obtained as the product of the early research which was performed on a parent nucleus having a structure similar to that of Proline (Pro), based on the fact that DPP-IV exhibits pronounced affinity for a peptide containing a certain amino acid Proline (Chinnaswamy T. et al., J. Biol. Chem., 1990, 1476-1483). Typical examples of Proline-like structures include pyrrolidide and thiazolidide, and derivatives containing these parent nucleus compounds exhibit reversible and competitive inhibitory activity for the DPP-IV enzyme (Augustyns K J L., et al., Eur. J. Med. Chem., 1997, 301-309).

Among products of such extensive research and development, there are continuing experiments on the action mechanism and efficacy of certain compounds, specifically Val-Pyr (Valine-Pyrrolidide), Ile-Thia (Isoleucine-Thiazolidide), and the like. Particularly, a great deal of attention has been focused on Ile-Thia, because the Val-Pyr structure exhibited relatively poor inhibitory activity on DPP-IV (Hanne B. R., et al., Nat. Struct. Biol., 2003, 19-25), which as such prompted intensive research and study on derivatives of the Ile-Thia compound.

Out of the Ile-Thia derivative compounds focused and obtained by the above-mentioned research and study, a compound having the most prominent activity was beta-amino acid thiazolidide series which was attempted to be developed by Merck & Co., Inc. However, according to the results of pharmacodynamic and pharmacokinetic experiments performed in rats, the obtained compound exhibited significantly low bioavailability in conjunction with an apparent limitation in the inhibition of enzymatic activity (Jinyou Xu, et al., Bioorg. Med. Chem. Lett., 2004, 4759-4762). As a consequence, further development on compounds of this class was discontinued due to profound disadvantages.

During the above-mentioned investigation, Merck noticed that a beta-amino acid, in addition to a thiazolidide parent nucleus, is also a key factor having significant effects on the DPP-IV inhibitory activity. This finding was applied to the approach for substitution of the thiazolidide parent nucleus with a different parent nucleus compound (Linda L. B., et al., Bioorg. Med. Chem. Lett., 2004, 4763-4766). With such a subsequent research, a variety of derivatives having substitution of the thiazolidide parent nucleus with a piperazine parent nucleus were synthesized with drug efficacy testing and pharmacodynamic studies. Unfortunately, the piperazine derivatives of Merck still suffered from significantly poor bioavailability. According to the compound optimization to cope with such a disadvantage, the product MK-0431 (trade name: JANUVIA) was developed with modification of a piperazine moiety to a triazolopiperazine moiety. This product is now commercially available under new drug approval by US FDA in 2006. Further, subsequent to MK-0431, a compound with incorporation of a diazepanone moiety (seven-membered ring) is currently under development (WO 2004037169; WO2005011581; WO2006104997; and Bioorg. Med. Chem. Lett., 2007, 49-52). Particularly according to the article published in the journal (Bioorg. Med. Chem. Lett., 2007, 49-52), it was demonstrated that imidazolone (five-membered ring) and piperazinone (six-membered ring) exhibit remarkably lower in vitro activity, as compared to diazepanone, thus resulting in an intensive focus on the optimization of diazepanone.

[MK-0431]

As a result of a variety of extensive and intensive studies and experiments to solve the problems as described above and to achieve the optimization of a compound of interest, the inventors of the present invention discovered that when a substitution including a hetero atom is made on a piperazinone moiety, the thus-modified compound not only has excellent DPP-IV inhibitory activity, but also is capable of achieving significantly improved bioavailability as compared to a conventional DPP-IV inhibitor, and then succeeded in synthesis of a novel heterocyclic compound containing a beta-amino group. The present invention has been completed based on these findings.

DISCLOSURE OF THE INVENTION

Technical Problem

It is an object of the present invention to provide a heterocyclic compound containing a beta-amino group and having DPP-IV inhibitory activity, or a pharmaceutically acceptable salt, hydrate or solvate thereof.

It is another object of the present invention to provide a pharmaceutical composition for the prevention and treatment of diabetes or obesity, comprising the aforesaid heterocyclic compound, or a pharmaceutically acceptable salt, hydrate or solvate thereof as an active ingredient.

Technical Solution

Hereinafter, the present invention will be described in more detail.

The present invention provides a heterocyclic compounds with a beta-amino group represented by Formula 1:

(1)

wherein X is OR1, SR1 or NR1R2 wherein R1 and R2 are independently $C_1$ to $C_5$ lower alkyl, and R1 and R2 of NR1R2 may form a 5 to 7-membered ring with inclusion of a hetero atom O; or a pharmaceutically acceptable salt thereof.

Preferably, the compound of Formula 1 in accordance with the present invention encompasses a compound of Formula 2, which is a stereoisomer inducing optical activity on a carbon atom at position 3 of a piperazinone ring and is represented by Formula 2 below.

(2)

wherein X is as defined in Formula 1.

That is, the compound of Formula 1 can have two asymmetric centers. Specifically, the compound of Formula 1, as shown Formula 2, can have asymmetric centers at the beta carbon and at carbon of position 3 of the piperazinone ring, so it can be present in the form of a single diastereoisomer, racemate, racemic mixture or diastereoisomeric mixture, all of which fall within the compound of Formula 1 in accordance with the present invention.

Further, the compound of Formula 1 can be partially present as a tautomer. Also included in the compound of Formula 1 are individual tautomers as well as mixtures thereof.

The stereoisomeric form of the compound of Formula 1 may be obtained by stereoselective synthesis according to a conventional method known in the art, using an optically pure starting material or a known reagent.

Preferred examples of the beta-amino group-containing heterocyclic compound of Formula 1 in accordance with the present invention may include the following compounds:

1) (R)-4-[(R)-3-amino-4-(2,4,5-trifluorophenyl)butanoyl]-3-(t-butoxymethyl)piperazin-2-one hydrochloride;
2) (R)-4-[(R)-3-amino-4-(2,4,5-trifluorophenyl)butanoyl]-3-(methoxymethyl)piperazin-2-one hydrochloride;
3) (R)-4-[(R)-3-amino-4-(2,4,5-trifluorophenyl)butanoyl]-3-(ethoxymethyl)piperazin-2-one hydrochloride;
4) (R)-4-[(R)-3-amino-4-(2,4,5-trifluorophenyl)butanoyl]-3-(isopropoxymethyl)piperazin-2-one hydrochloride;
5) (R)-4-[(R)-3-amino-4-(2,4,5-trifluorophenyl)butanoyl]-3-(cyclopentyloxymethyl)piperazin-2-one hydrochloride;
6) (R)-4-[(R)-3-amino-4-(2,4,5-trifluorophenyl)butanoyl]-3-[(diethylamino)methyl]piperazin-2-one dihydrochloride;
7) (R)-4-[(R)-3-amino-4-(2,4,5-trifluorophenyl)butanoyl]-3-[(ethylmethylamino)methyl]piperazin-2-one dihydrochloride;
8) (R)-4-[(R)-3-amino-4-(2,4,5-trifluorophenyl)butanoyl]-3-(morpholinomethyl)piperazin-2-one dihydrochloride;
9) (R)-4-[(R)-3-amino-4-(2,4,5-trifluorophenyl)butanoyl]-3-(t-butylthiomethyl)piperazin-2-one hydrochloride;
10) (S)-4-[(R)-3-amino-4-(2,4,5-trifluorophenyl)butanoyl]-3-(t-butoxymethyl)piperazin-2-one hydrochloride;
11) (R)-4-[(R)-3-amino-4-(2,4,5-trifluorophenyl)butanoyl]-3-(t-butoxymethyl)piperazin-2-one;
12) (R)-4-[(R)-3-amino-4-(2,4,5-trifluorophenyl)butanoyl]-3-(t-butoxymethyl)piperazin-2-one tartrate;
13) (R)-4-[(R)-3-amino-4-(2,4,5-trifluorophenyl)butanoyl]-3-(t-butoxymethyl)piperazin-2-one citrate;
14) (R)-4-[(R)-3-amino-4-(2,4,5-trifluorophenyl)butanoyl]-3-(t-butoxymethyl)piperazin-2-one phosphate;
15) (R)-4-[(R)-3-amino-4-(2,4,5-trifluorophenyl)butanoyl]-3-(t-butoxymethyl)piperazin-2-one acetate;
16) (R)-4-[(R)-3-amino-4-(2,4,5-trifluorophenyl)butanoyl]-3-(t-butoxymethyl)piperazin-2-one malate;
17) (R)-4-[(R)-3-amino-4-(2,4,5-trifluorophenyl)butanoyl]-3-(t-butoxymethyl)piperazin-2-one succinate; and
18) (R)-4-[(R)-3-amino-4-(2,4,5-trifluorophenyl)butanoyl]-3-(t-butoxymethyl)piperazin-2-one adipate.

The beta-amino group-containing heterocyclic compound of Formula 1 in accordance with the present invention includes a pharmaceutically acceptable salt thereof as well as a hydrate and solvate that can be prepared therefrom.

The pharmaceutically acceptable salt of the heterocyclic compound of Formula 1 may be prepared by any conventional method for preparation of salts known in the art.

As used herein, the term "pharmaceutically acceptable salt" refers to a salt prepared from a pharmaceutically acceptable non-toxic base or acid including an inorganic or organic base and an inorganic or organic acid. Examples of the pharmaceutically acceptable salt may include salts of Compound 1 with an inorganic base, e.g. aluminum, ammonium, calcium, copper, ferric, ferrous, lithium, magnesium, manganate, manganese, potassium, sodium or zinc ion. Particularly preferred are ammonium, calcium, magnesium, potassium and sodium salts. A solid salt may have one or more crystal structures, or otherwise may be in the form of a hydrate. Examples of the pharmaceutically acceptable non-toxic organic salt may include salts of Compound 1 with a primary, secondary or tertiary amine, a substituted amine such as a naturally-occurring substituted amine, a cyclic amine, or a basic ion exchange resin such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resin, procaine, purine, theobromine, triethylamine, trimethylamine, tripropylamine, and tromethamine.

When the compound of the present invention is basic, a salt thereof may be prepared from pharmaceutically acceptable non-toxic acids including inorganic and organic acids. Examples of the acid may include acetic acid, benzenesulfonic acid, benzoic acid, camphorsulfonic acid, citric acid, ethanesulfonic acid, fumaric acid, gluconic acid, glutamic acid, hydrobromic acid, hydrochloric acid, isethionic acid, lactic acid, maleic acid, malic acid, mandelic acid, methanesulfonic acid, mucic acid, nitric acid, pamoic acid, pantothenic acid, phosphoric acid, succinic acid, sulfuric acid, tartaric acid, p-toluene sulfonic acid, and adipic acid. Particularly preferred are acetic, citric, hydrochloric, malic, phosphoric, succinic, tartaric and adipic acids.

When the compound of Formula 1 is designated herein, this term is intended to embrace a pharmaceutically acceptable salt thereof.

As used herein, the term "hydrate" means a compound of Formula 1 or a pharmaceutically acceptable salt thereof, which further includes a stoichiometric or non-stoichiometric amount of water bound thereto by non-covalent intermolecular forces. The hydrate may contain more than 1 equivalent of water, typically 1 to 5 equivalents of water. The hydrate may be prepared by crystallization of the compound of Formula 1 or a pharmaceutically acceptable salt thereof in water or water-containing solvent.

As used herein, the term "solvate" means a compound of Formula 1 or a salt thereof, which further includes a stoichiometric or non-stoichiometric amount of a solvent bound thereto by non-covalent intermolecular forces. Preferred solvents are volatile, non-toxic, and/or acceptable for administration to humans. For example, mention may be made of ethanol, methanol, propanol, methylene chloride, etc.

In accordance with another aspect of the present invention, there is provided a method for preparing a heterocyclic compound with a beta-amino group represented by Formula 1 or a pharmaceutically acceptable salt thereof.

The present invention, as shown in Reaction Scheme 1 below, includes a method for preparing a heterocyclic compound represented by Formula 2, comprising 1) reacting a compound of Formula 3 having a beta amino group with a substituted heterocyclic compound of Formula 4 in the presence of 1-hydroxybenzotriazole (HOBT), 1-ethyl-3-(3-dimethylaminopropyl)carbodiimide (EDC) and tertiary amine to thereby prepare a compound of Formula 5 having a peptide bond, and 2) reacting the compound of Formula 5 in the presence of an acid to prepare a heterocyclic compound of Formula 2 having a beta-amino group.

wherein X is as defined in Formula 1.

For example, an intermediate of Formula 5 may be obtained by reacting the compound of Formula 3 and the compound of Formula 4 conventionally in a solvent such as N,N-dimethylformamide (DMF) or dichloromethane in the presence of a coupling reagent such as 1-ethyl-3-(3-dimethylaminopropyl)carbodiimide (EDC) or 1-hydroxybenzotriazole (HOBT), and a base such as diisopropylethylamine or triethylamine at 0° C. to room temperature for 3 to 48 hours.

In order to prevent participation of a compound in peptidization, a nitrogen atom of the intermediate of Formula 5 which was prepared by peptidization is protected with a protective group. The desired heterocyclic compound of Formula 2 having a beta-amino group may be obtained by removal of the protective group through deprotection. That is, because the protective group is Boc, removal of the protective group may be carried out under acidic conditions, typically using trifluoroacetic acid/dichloromethane, ethyl acetate/hydrogen chloride, hydrogen chloride/dichloromethane or methanol/hydrogen chloride, at 0° C. to room temperature for 1 to 24 hours.

If necessary, the compound of Formula 2 prepared by the peptide bond reaction and deprotection may be purified from undesirable by-products by any conventional method such as recrystallization, trituration, preparative thin-layer chromatography, silica gel flash chromatography (see W. C. Still et al., J. Org. Chem., 43, 2923 (1978)), or HPLC. The compound purified by HPLC may be separated as the corresponding salt thereof. The compound of Formula 5 can also be purified in the same manner.

In the present invention, a stereoisomeric mixture of a compound of Formula 1 is prepared by using a mixture of stereoisomers as a starting material, and the resulting mixture is separated into individual stereoisomers to thereby obtain a compound of Formula 1. Further, each stereoisomer of the compound of Formula 1 may be prepared by using each stereoisomer as a starting material. Separation of the stereoisomer may be carried out by conventional column chromatography or recrystallization.

In the preparation of the compound of Formula 2, the compound of Formula 3 used in Reaction Scheme 1 is commercially available or may be readily prepared by any method known in the art.

In the preparation of the compound of Formula 2, the compound of Formula 4 used in Reaction Scheme 1 may be prepared according to the synthetic pathway of Reaction Scheme 2 and Reaction Scheme 3.

In Reaction Scheme 2, Compound 6 may be commercially available or may not be commercially available depending on a substituent X, so Compound 6 is commercially available one or may be readily prepared by any method known in the art, for example the method as depicted in Reaction Scheme 3 below.

In Reaction Scheme 2, Compound 4 used to prepare the compound of the present invention can be prepared from Compound 6. Specifically, Compound 6 is reacted with N-butyloxycarbonyl-2-amino acetaldehyde in the presence of a reducing agent to obtain Compound 7 from which Compound 8 having a secondary amine protected by benzyloxycarbonyl (Cbz) is then prepared, followed by deprotection to thereby prepare Compound 9 where butyloxycarbonyl (Boc) was deprotected. Compound 9 is then cyclized using trimethyl aluminum (or diisopropylethylamine/ethanol, sodium hydrogen carbonate/methanol, etc.) to obtain Compound 10 which is followed by deprotection of Cbz to prepare Compound 4. Examples of the reducing agent that can be used in the preparation of Compound 7 from Compound 6 may include sodium cyanoborohydride, sodium triacetoxyborohydride, sodium borohydride, and the like.

[Reaction Scheme 2]

wherein X is as defined in Formula 1.

When Compound 6 in Reaction Scheme 2 is not commercially available, it may be prepared analogously to Reaction Scheme 3 below. Compound 6 having a variety of substituents R1 in Reaction Scheme 3 is prepared by substituting D-serine methyl ester with trityl chloride to obtain Compound 11, and substituting a hydroxyl group of Compound 11 with a mesyl group, followed by reflux to thereby prepare an aziridine compound 12. Then, the trityl group of Compound 12 is removed using trifluoroacetic acid, followed by benzyloxycarbonyl (Cbz) protection to prepare Compound 13. Compound 13 is then reacted with HX having a variety of substituents R1 to prepare Compound 14, followed by Cbz deprotection to prepare Compound 6.

wherein X is as defined in Formula 1.

In order to facilitate the reaction of interest or avoid formation of the undesired reaction product for some of compounds of Formula 1 of the present invention, the aforementioned reaction conditions and reaction sequences may vary as desired.

As described above, compounds of Formula 1 of the present invention, starting materials and intermediates may be synthesized by a variety of methods known in the art.

In accordance with a further aspect of the present invention, there is provided a pharmaceutical composition for the prevention and treatment of diabetes or obesity, comprising a compound of Formula 1 or a pharmaceutically acceptable salt thereof as an active ingredient.

The compound of Formula 1 in accordance with the present invention exhibits excellent inhibitory activity on DPP-IV. When inhibitory capacity of the compound of Formula 1 on the enzyme DPP-IV was measured, $IC_{50}$, the concentration of drug that is required to inhibit the enzymatic reaction of DPP-IV by 50%, almost exhibits a range of 0.5 to 20 nM, which represents superior DPP-IV inhibitory activity, as compared to a conventional DPP-IV inhibitor reported to have $IC_{50}$ of several hundreds of nM to several thousands of nM, or to even several tens of thousands of nM (Jinyou Xu, et al., Bioorg. Med. Chem. Lett., 2004, 4759-4762; and Linda L. B., et al., Bioorg. Med. Chem. Lett., 2004, 4763-4766).

Further, the compound of Formula 1 in accordance with the present invention has high oral glucose tolerance. According to the oral glucose tolerance test (OGTT), the compound of Formula 1 was measured to have blood glucose-lowering effects of more than 35%, preferably more than 50%, thus representing that it has superior bioavailability as compared to conventional DPP-IV inhibitors. In addition, in vivo experimental results, including pharmacokinetic/pharmacodynamic correlations, measurement of a duration period of DPP-IV inhibitory activity, and in vivo kinetic experiments, demonstrate that the compound of the present invention is superior in DPP-IV inhibitory activity and bioavailability.

Therefore, the pharmaceutical composition comprising the compound of Formula 1 as an active ingredient may be effectively used for the treatment and prevention of diabetes and obesity which are representative diseases caused by DPP-IV.

In accordance with yet another aspect of the present invention, there is provided a use of the aforesaid composition for the prevention and treatment of diabetes or obesity, and a method for the prevention and treatment of diabetes or obesity, comprising administering an effective amount of the aforesaid composition to a mammal (including human).

The pharmaceutical composition comprising the compound of Formula 1, or a stereoisomer, pharmaceutically acceptable salt, hydrate or solvate thereof as an active ingredient may be formulated into a variety of the following oral or parenteral dosage forms without being limited thereto.

Examples of the dosage form for oral administration may include tablets, pills, soft and hard capsules, solutions, suspensions, emulsions, syrups, granules, elixirs, and the like. These pharmaceutical formulations may comprise, in addition to the aforesaid active ingredient, one or more conventional diluents or excipients, such as fillers, extenders, wetting agents, disintegrants, glidants, binders, and surfactants. Examples of the disintegrants may include agar, starch, alginic acid or a sodium salt thereof, anhydrous calcium monohydrogen phosphate, and the like. Examples of the glidants may include silica, talc, stearic acid or a magnesium or calcium salt thereof, polyethylene glycol, and the like. Examples of the binder may include magnesium aluminum silicate, starch paste, gelatin, tragacanth, methylcellulose, sodium carboxymethylcellulose, polyvinylpyrrolidone, low-substituted hydroxypropyl cellulose, and the like. In addition, the pharmaceutical formulation may comprise diluents, e.g. lactose, dextrose, sucrose, mannitol, sorbitol, cellulose and/or glycine. If desired, the formulation may further comprise conventionally known effervescent mixtures, absorbents, colorants, flavors and sweeteners.

The pharmaceutical composition comprising the compound of Formula 1 or a pharmaceutically acceptable salt thereof as an active ingredient may be administered via a parenteral route, for example a suppository, subcutaneous injection, intravenous injection, intramuscular injection or intrathoracic injection. For formulation of the composition of the present invention into a preparation for parental administration, the compound of Formula 1 or a pharmaceutically acceptable salt thereof is mixed with a stabilizer or buffer in the presence of water to prepare a solution or suspension which is then manufactured in the unit dosage form of ampoules or vials.

The composition may be sterilized and/or comprise adjuvants such as preservatives, stabilizers, hydrating agents, emulsifiers, salts for controlling osmotic pressure, and/or buffers, and therapeutically useful substances, and can be formulated according to conventional methods such as mixing, granulation and coating.

If desired, the compound of Formula 1 or the pharmaceutical composition comprising the same as an active ingredient may be administered in combination with other drugs, for example, anti-diabetic drugs.

When the compound of Formula 1 or the pharmaceutical composition comprising the same as an active ingredient is formulated into a unit dosage form, the compound of Formula 1 is applied preferably in a unit dose of approx. 0.1 to 1,500 mg in terms of active ingredient. As will be apparent to those skilled in the art, the effective dose of the active compound in accordance with the present invention may be determined according to physician's prescription, depending on various factors such as body weight and age of patients, the nature and severity of disease, and the like. For adults, the effective dose of the active compound is typically in a range of about 1 to 500 mg/day, taking into consideration administration frequency and intensity. In case of intramuscular or intravenous injection to adults, about 5 to 300 mg of the total dose divided into several unit doses may be appropriate a day, even though a higher daily dose may be required for some patients.

Advantageous Effects

As will be specifically illustrated hereinafter, the present invention provides a heterocyclic compound containing a beta-amino group and having excellent inhibitory effects on the enzymatic activity of DPP-IV. A pharmaceutical composition comprising the same compound of the present invention as an active ingredient exhibits excellent DPP-IV inhibitory activity and bioavailability and then can be useful for the prophylaxis or treatment of various diseases considered to be caused by DPP-IV, such as diabetes and obesity.

MODE FOR INVENTION

Now, the present invention will be described in more detail with reference to the following Examples. These examples are provided only for illustrating the present invention and should not be construed as limiting the scope and spirit of the present invention.

Example 1

Preparation of (R)-4-[(R)-3-amino-4-(2,4,5-trifluorophenyl)butanoyl]-3-(t-butoxymethyl)piperazin-2-one hydrochloride Step 1: Preparation of (R)-methyl 1-tritylaziridine-2-carboxylate 200 g of D-serine methyl ester hydrochloride was added to 1.8 L of chloroform, and the reaction solution was cooled to 0° C., to which 448 mL of triethylamine was then slowly added. 358.4 g of trityl chloride was slowly added to the reaction mixture which was then stirred for 1 hour. The reaction mixture was warmed to room temperature, and 1 L of chloroform was added thereto, followed by washing with 2.5 L of water. The organic layer was dried over magnesium sulfate and cooled to 0° C., to which 484 mL of triethylamine and 15.7 g of 4-methylaminopyridine were then sequentially and slowly added. The reaction mixture was stirred for 5 min and 139 mL of methane sulfonyl chloride was slowly added thereto. The reaction mixture was warmed to room temperature, stirred for another 4 hours and then refluxed for 12 hours. The reaction mixture was cooled to room temperature, and washed with 4 L of water and then 3 L of brine. The organic layer was dried over magnesium sulfate and concentrated to dryness under reduced pressure. 3 L of ethanol was added to the resulting residue which was then stirred. The resulting solids were filtered to afford 329 g of the title compound.

1H NMR (400 MHz, CDCl3): 7.42 to 7.49 (m, 6H), 7.18 to 7.32 (m, 9H), 7.68 (s, 1H), 3.74 (s, 3H), 2.24 (m, 1H), 1.87 (m, 1H), and 1.40 (m, 1H)

Step 2: Preparation of (R)-1-benzyl 2-methyl aziridine-1,2-dicarboxylate 328.4 g of (R)-methyl 1-tritylaziridine-2-carboxylate was dissolved in 1.4 L of chloroform and the reaction solution was cooled to 0° C., to which 462 mL of trifluoroacetic acid was then slowly added. The reaction mixture was stirred for 1 hour, to which 2 L of water was then added, followed by stirring for 10 min and removal of the organic layer. The aqueous layer was neutralized with sodium hydrogen carbonate and used in subsequent reactions without further purification.

2 L of diethyl ether and 120.5 g of sodium hydrogen carbonate were added to the aqueous layer, and the reaction solution was cooled to 0° C., to which 165 mL of benzyl chloroformate was then slowly added dropwise. The reaction mixture was stirred for another 2 hours and the aqueous layer was discarded. The organic layer was dried over magnesium sulfate, concentrated and dried under reduced pressure, and purified by column chromatography, thereby affording 108.5 g of the title compound.

1H NMR (400 MHz, DMSO): 7.32-7.36 (m, 5H), 5.13 (s, 2H), 3.09 (dd, J=3.2, 5.4 Hz, 1H), 2.58 (dd, J=1.2, 3.2 Hz, 1H), and 2.47 (dd, J=1.2, 5.4 Hz, 1H)

Step 3: Preparation of (R)-2-amino-3-t-butoxypropane methyl ester 1.1 g of (R)-1-benzyl 2-methyl aziridine-1,2-dicarboxylate was dissolved in 11 mL of chloroform, to which 18 mL of t-butanol was then added. To the reaction mixture was slowly added dropwise 1.2 mL of $BF_3OEt_2$, followed by stirring for 12 hours. The reaction was terminated with addition of 2 L of water to the reaction mixture. Then, the organic layer was separated and dried over magnesium sulfate, concentrated and dried under reduced pressure, and then used in subsequent reactions without further purification.

The resulting residue was dissolved in 10 mL of methanol, to which 740 mg of palladium/carbon in 2 mL of ethyl acetate was then added, followed by hydrogen bubbling for 1 hour under ambient atmospheric pressure. The reaction mixture was filtered and dried under reduced pressure to afford 736 mg of the title compound.

1H NMR (400 MHz, CD3OD): 4.21 (m, 1H), 3.82 (s, 3H), 3.74-3.88 (m, 2H), and 1.20 (s, 9H)

Step 4): Preparation of (R)-3-tert-butoxy-2-(2-(tert-butoxycarbonylamino) ethylamino)propionic acid methyl ester 736 mg of (R)-2-amino-3-t-butoxypropane methyl ester prepared in Step 3 was dissolved in 14 mL of dichloromethane, to which 6335 mg of N-t-butoxycarbonyl-2-aminoacetaldehyde methanol was then slowly added. The reaction mixture was cooled to 0° C., followed by gradual addition of 1.2 mL of triethylamine and 1.78 g of sodium triacetoxyborohydride. The reaction mixture was warmed to room temperature, followed by stirring for 12 hours. A saturated sodium hydrogen carbonate solution was added to terminate the reaction, and the organic layer was washed with 10 mL of water and brine, concentrated and dried under reduced pressure. The resulting residue was purified by column chromatography, thereby affording 355 mg of the title compound.

1H NMR (400 MHz, CDCl3): 5.10 (m, 1H), 3.71 (s, 3H), 3.56 (m, 2H), 3.40 (m, 1H), 3.15-3.28 (m, 2H), 2.81 (m, 1H), 2.67 (m, 1H), 1.42 (s, 9H), and 1.13 (s, 9H)

Step 5): Preparation of (R)-2-((benzyloxycarbonyl) (2-t-butoxycarbonylamino) ethyl)amino)-3-tert-butoxypropionic acid methyl ester 355 mg of (R)-3-tert-butoxy-2-(2-(tert-butoxycarbonylamino)ethylamino)propionic acid methyl ester prepared in Step 4 was dissolved in 11 mL of tetrahydrofuran, and the reaction mixture was cooled to 0° C., to which 187 mg of sodium hydrogen carbonate was then added. 192 µl of benzylchloroformate was slowly added dropwise thereto, and the reaction mixture was warmed to room temperature. After 12 hours, the reaction mixture was dried under reduced pressure, followed by addition of 10 mL of ethyl acetate, and the organic layer was washed with 10 mL of water. The organic layer was dried over magnesium sulfate, dried under reduced pressure, and purified by column chromatography, thereby affording 410 mg of the title compound.

1H NMR (400 MHz, CDCl3): 7.36-7.25 (m, 5H), 5.82-5.72 (m, 1H), 5.17-5.03 (m, 2H), 4.15 (m, 1H), 3.98 (m, 1H), 3.81 (m, 1H), 3.73 (s, 3H), 3.60 (m, 1H), 3.42-3.28 (m, 3H), 1.40 (s, 9H), and 1.14 (s, 9H)

Step 6): Preparation of (R)-benzyl 2-(tert-butoxymethyl)-3-oxopiperazine-1-carboxylate 410 mg of (R)-2-((benzyloxycarbonyl)(2-t-butoxycarbonylamino)ethyl)amino)-3-tert-butoxypropionic acid methyl ester prepared in Step 5 was dissolved in 10 mL of methanol, and the reaction mixture was cooled to 0° C., to which 4 mL of 2-N hydrochloric acid/diethyl ether was then slowly added, followed by stirring for 3 hours. The reaction mixture was dried under reduced pressure and used in subsequent reactions without further purification.

The resulting residue was dissolved in 10 mL of dichloromethane and the reaction mixture was cooled to 0° C., to which 152 µl of triethylamine was then slowly added. 1.1 mL of trimethylaluminum (2.0 M solution in toluene) was slowly added thereto, and the reaction mixture was warmed to room temperature and then stirred for 12 hours. The reaction mixture was cooled to 0° C. and a saturated ammonium chloride aqueous solution was added to terminate the reaction. 10 mL of ethyl acetate was added to the reaction mixture which was then washed with 10 mL of brine. The organic layer was dried over magnesium sulfate and dried under reduced pressure. The resulting residue was purified by column chromatography to afford 103 mg of the title compound.

1H NMR (400 MHz, CDCl3): 7.34-7.25 (m, 5H), 6.27 (m, 1H), 5.14 (m, 2H), 4.57 (m, 1H), 4.19 (m, 1H), 4.08 (m, 1H), 3.94 (m, 1H), 3.74 (m, 1H), 3.64 (m, 1H), 3.42 (m, 1H), 3.29 (m, 1H), and 1.09 (s, 9H)

Step 7): Preparation of (R)-(3-tert-butoxymethyl)piperazin-2-one 103 mg of (R)-benzyl 2-(tert-butoxymethyl)-3-oxopiperazine-1-carboxylate prepared in Step 6 was dissolved in 2 mL of methanol, to which 50 mg of palladium/carbon in 1 mL of ethyl acetate was then added, followed by hydrogen bubbling for 1 hour under ambient atmospheric pressure. The reaction mixture was filtered and dried under reduced pressure to afford 58 mg of the title compound.

1H NMR (400 MHz, CDCl3): 6.41 (brs, 1H), 3.76 (m, 3H), 3.63 (m, 1H), 3.52 (m, 1H), 3.42 (m, 1H), 3.28 (m, 1H), 3.16 (m, 1H), 2.95 (m, 1H), 2.45 (brs, 1H), and 1.17 (s, 9H)

Step 8): Preparation of tert-butyl (R)-4-[(R)-2-(tert-butoxymethyl)-3-oxopiperazin-1-yl]-4-oxo-1-(2,4,5-trifluorophenyl)butan-2-ylcarbamate 104 mg of (3R)-t-butoxycarbonylamino-4-(2,4,5-trifluorophenyl)butanoic acid and 58 mg of (R)-(3-tert-butoxymethyl)piperazin-2-one were added to 4 mL of N,N-dimethylformamide, to which 63 mg of 1-hydroxybenzotriazole (HOBT) and 217 µl of diisopropylethylamine were then added. The reaction mixture was cooled to 0° C. and 78 mg of 1-ethyl-3-(3-dimethylaminopropyl)carbodiimide (EDC) was added thereto, followed by stirring at room temperature for 12 hours. The reaction mixture was diluted with 10 mL of ethyl acetate and washed two times with brine. The organic layer was dried over magnesium sulfate and concentrated. The resulting residue was purified by column chromatography to afford 97 mg of the title compound.

1H NMR (400 MHz, CDCl3): 7.03 (m, 1H), 6.88 (m, 1H), 5.97 (m, 1H), 5.48 (m, 1H), 4.16-4.07 (m, 1H), 4.02-3.91 (m, 1H), 3.74 (m, 2H), 3.37 (m, 2H), 3.24 (m, 1H), 2.92 (m, 2H), 2.80 (m, 1H), 2.59 (m, 2H), 1.34 (d, 9H), and 1.13 (s, 9H)

Step 9): Preparation of (R)-4-[(R)-3-amino-4-(2,4,5-trifluorophenyl)butanoyl]-3-(tert-butoxymethyl)piperazin-2-one hydrochloride 97 mg of tert-butyl (R)-4-[(R)-2-(tert-butoxymethyl)-3-oxopiperazin-1-yl]-4-oxo-1-(2,4,5-trifluorophenyl)butan-2-ylcarbamate prepared in Step 8 was dissolved in 3 mL of methanol, followed by addition of 2 mL of 2N-hydrochloric acid/diethyl ether and stirring at room temperature for 3 hours. The reaction mixture was concentrated and dried under reduced pressure to afford 64 mg of the title compound as a foamy solid.

1H NMR (400 MHz, CD3OD): 7.37 (m, 1H), 7.23 (m, 1H), 4.80 (m, 1H), 4.59-4.40 (m, 1H), 3.93 (m, 1H), 3.90-3.83 (m, 2H), 3.70 (m, 1H), 3.38 (m, 2H), 3.27 (m, 1H), 3.07 (m, 2H), 2.89-2.66 (m, 2H), 1.18 (s, 3H), and 1.11 (s, 6H)

Mass (M+1): 402

Example 2

Preparation of (R)-4-[(R)-3-amino-4-(2,4,5-trifluorophenyl)butanoyl]-3-(methoxymethyl)piperazin-2-one hydrochloride Methanol was used instead of t-butanol in Step 3 of Example 1, and 40 mg of the title compound was then synthesized analogously to Steps 4 through 9 of Example 1.

1H NMR (400 MHz, CD3OD): 7.34 (m, 1H), 7.23 (m, 1H), 4.82 (m, 1H), 4.62-4.46 (m, 1H), 3.92 (m, 1H), 3.87-3.82 (m, 2H), 3.66 (m, 1H), 3.35 (m, 2H), 3.24 (m, 1H), 3.04 (m, 2H), 2.94-2.72 (m, 2H), and 3.27 (s, 3H)

Mass (M+1): 360

Example 3

Preparation of (R)-4-[(R)-3-amino-4-(2,4,5-trifluorophenyl)butanoyl]-3-(ethoxymethyl)piperazin-2-one hydrochloride Ethanol was used instead of t-butanol in Step 3 of Example 1, and 66 mg of the title compound was then synthesized analogously to Steps 4 through 9 of Example 1.

1H NMR (400 MHz, CD3OD): 7.38 (m, 1H), 7.23 (m, 1H), 4.83 (m, 1H), 4.54-4.44 (m, 1H), 3.98 (m, 1H), 3.93-3.82 (m, 2H), 3.71 (m, 1H), 3.53 (m, 2H), 3.36 (m, 2H), 3.26 (m, 1H), 3.07 (m, 2H), 2.90-2.70 (m, 2H), and 1.11 (t, 3H)

Mass (M+1): 374

Example 4

Preparation of (R)-4-[(R)-3-amino-4-(2,4,5-trifluorophenyl)butanoyl]-3-(isopropoxymethyl)piperazin-2-one hydrochloride Isopropanol was used instead of t-butanol in Step 3 of Example 1, and 69 mg of the title compound was then synthesized analogously to Steps 4 through 9 of Example 1.

1H NMR (400 MHz, CD3OD): 7.38 (m, 1H), 7.23 (m, 1H), 4.86 (m, 1H), 4.62-4.43 (m, 1H), 3.96 (m, 1H), 3.90-3.87 (m, 2H), 3.77 (m, 1H), 3.69 (m, 1H), 3.44 (m, 2H), 3.26 (m, 1H), 3.08 (m, 2H), 2.95-2.69 (m, 2H), and 1.15 (m, 6H)

Mass (M+1): 388

Example 5

Preparation of (R)-4-[(R)-3-amino-4-(2,4,5-trifluorophenyl)butanoyl]-3-(cyclopentyloxymethyl)piperazin-2-one hydrochloride Cyclopentanol was used instead of t-butanol in Step 3 of Example 1, and 51 mg of the title compound was then synthesized analogously to Steps 4 through 9 of Example 1.

1H NMR (400 MHz, CD3OD): 7.38 (m, 1H), 7.23 (m, 1H), 4.82 (m, 1H), 4.61-4.42 (m, 1H), 3.93 (m, 1H), 3.90-3.82 (m, 2H), 3.67 (m, 1H), 3.40 (m, 1H), 3.36 (m, 2H), 3.25 (m, 1H), 3.08 (m, 2H), 3.01-2.62 (m, 2H), and 1.67-1.50 (m, 8H)

Mass (M+1): 414

Example 6

Preparation of (R)-4-[(R)-3-amino-4-(2,45-trifluorophenyl)butanoyl]-3-[(diethylamino)methyl]piperazin-2-one dihydrochloride Diethylamine was added instead of t-butanol and reflux was carried out instead of addition of $BF_3OEt_2$ in Step 3 of Example 1, and 68 mg of the title compound was then synthesized analogously to Steps 4 through 9 of Example 1.

1H NMR (400 MHz, CD3OD): 7.41 (m, 1H), 7.24 (m, 1H), 5.21 (m, 1H), 3.59-3.53 (m, 2H), 3.50-3.53 (m, 4H), 3.43-3.37 (m, 4H), 3.35 (m, 2H), 3.09 (m, 2H), 2.97-2.81 (m, 2H), and 1.37 (m, 6H)

Mass (M+1): 401

Example 7

Preparation of (R)-4-[(R)-3-amino-4-(2,4,5-trifluorophenyl)butanoyl]-3-[(ethylmethylamino)methyl]piperazin-2-one dihydrochloride Ethylmethylamine was added instead of t-butanol and reflux was carried out instead of addition of $BF_3OEt_2$ in Step 3 of Example 1, and 67 mg of the title compound was then synthesized analogously to Steps 4 through 9 of Example 1.

1H NMR (400 MHz, CD3OD): 7.42 (m, 1H), 7.24 (m, 1H), 5.22 (m, 1H), 4.08-3.87 (m, 2H), 3.86-3.75 (m, 2H), 3.68-3.57 (m, 2H), 3.56-3.33 (m, 4H), 3.09 (m, 2H), 3.02-2.81 (m, 5H), and 1.38 (m, 3H)

Mass (M+1): 387

Example 8

Preparation of (R)-4-[(R)-3-amino-4-(2,4,5-trifluorophenyl)butanoyl]-3-(morpholinomethyl)piperazin-2-one dihydrochloride Morpholine was added instead of t-butanol and reflux was carried out instead of addition of $BF_3OEt_2$ in Step 3 of Example 1, and 27 mg of the title compound was then synthesized analogously to Steps 4 through 9 of Example 1.

1H NMR (400 MHz, CD3OD): 7.37 (m, 1H), 7.23 (m, 1H), 5.32 (m, 1H), 4.12-3.98 (m, 4H), 3.97-3.77 (m, 4H), 3.74-3.52 (m, 4H), 3.48-3.39 (m, 2H), 3.14-2.91 (m, 4H), and 2.86-2.72 (m, 2H)

Mass (M+1): 415

Example 9

Preparation of (R)-4-[(R)-3-amino-4-(2,4,5-trifluorophenyl)butanoyl]-3-(t-butylthiomethyl)piperazin-2-one hydrochloride t-butyl thiol was used instead of t-butanol in Step 3 of Example 1, and 25 mg of the title compound was then synthesized analogously to Steps 4 through 9 of Example 1.

1H NMR (400 MHz, CD3OD): 7.34 (m, 1H), 7.25 (m, 1H), 5.04 (m, 1H), 4.60 (s, 1H), 4.60-4.41 (m, 1H), 3.86 (m, 2H), 3.70 (m, 1H), 3.40 (m, 2H), 3.25 (m, 1H), 3.05 (m, 2H), 2.95 (m, 1H), 2.81 (m, 2H), and 1.26 (s, 9H)

Mass (M+1): 418

Example 10

Preparation of (S)-4-[(R)-3-amino-4-(2,4,5-trifluorophenyl)butanoyl]-3-(t-butoxymethyl)piperazin-2-one hydrochloride L-serine methyl ester hydrochloride was used instead of D-serine methyl ester hydrochloride in Step 1 of Example 1, and 31 mg of the title compound was then synthesized analogously to Steps 2 through 9 of Example 1.

1H NMR (400 MHz, CD3OD): 7.34 (m, 1H), 7.24 (m, 1H), 4.79 (m, 1H), 4.580-4.40 (m, 1H), 3.96 (m, 1H), 3.86-3.74 (m, 2H), 3.70 (m, 1H), 3.36 (m, 2H), 3.19 (m, 1H), 3.05-2.86 (m, 3H), 2.67 (m, 1H), 1.15 (s, 4H), and 1.03 (s, 5H)

Mass (M+1): 402

Example 11

Preparation of (R)-4-[(R)-3-amino-4-(2,4,5-trifluorophenyl) butanoyl]-3-(t-butoxymethyl)piperazin-2-one 60 mg of the compound obtained in Example 1 was added to 10 mL of a 5% sodium hydrogen carbonate aqueous solution, and the mixture was extracted two times with 10 mL of a mixed solution of dichloromethane/2-propanol (4/1(v/v)). The organic layer was dried under reduced pressure to afford 55 mg of the title compound as a solid.

1H NMR (400 MHz, CD3OD): 7.27 (m, 1H), 7.14 (m, 1H), 4.56-4.39 (m, 1H), 3.96-3.81 (m, 3H), 3.70 (m, 1H), 3.46 (m, 1H), 3.43-3.32 (m, 1H), 2.83-2.65 (m, 3H), 2.58-2.40 (m, 2H), 1.16 (s, 3H), and 1.11 (s, 6H)

Mass (M+1): 402

Example 12

Preparation of (R)-4-[(R)-3-amino-4-(2,4,5-trifluorophenyl)butanoyl]-3-(t-butoxymethyl)piperazin-2-one tartrate 55 mg of the compound obtained in Example 11 was dissolved in 0.56 mL of acetone to which a solution of 26 mg of L-tartaric acid in 0.35 mL of ethanol/water (9/1(v/v)) was then slowly added, followed by stirring for 30 min. 0.56 mL of 2-propanol was added thereto, followed by stirring for 10 min and filtration to afford 77 mg of the title compound as a solid.

1H NMR (400 MHz, CD3OD): 7.38 (m, 1H), 7.22 (m, 1H), 4.80 (m, 1H), 4.59-4.40 (m, 1H), 4.40 (s, 2H), 3.93 (m, 1H), 3.90-3.83 (m, 2H), 3.70 (m, 1H), 3.38 (m, 2H), 3.27 (m, 1H), 3.07 (m, 2H), 2.89-2.66 (m, 2H), 1.15 (s, 3H), and 1.11 (s, 6H)

Mass (M+1): 402

Example 13

Preparation of (R)-4-[(R)-3-amino-4-(2,4,5-trifluorophenyl)butanoyl]-3-(t-butoxymethyl)piperazin-2-one citrate 496 mg of the compound obtained in Example 11 was dissolved in 2 mL of ethanol, to which a solution of 273 mg of anhydrous citric acid in 1 mL of water was then slowly added, followed by stirring for 30 min. The reaction mixture was concentrated, to which 2 mL of ethyl acetate and 1 mL of 2-propanol were then added followed by stirring. 15 mL of hexane was added thereto followed by stirring for 10 min and filtration to afford 637 mg of the title compound as a solid.

1H NMR (400 MHz, CD3OD): 7.34 (m, 1H), 7.22 (m, 1H), 4.81 (m, 1H), 4.58-4.40 (m, 1H), 3.94 (m, 1H), 3.87 (m, 2H), 3.70 (m, 1H), 3.36 (m, 2H), 3.25 (m, 1H), 3.03 (m, 2H), 2.94-2.70 (m, 4H), 1.18 (s, 3H), and 1.12 (s, 6H)

Mass (M+1): 402

Example 14

Preparation of (R)-4-[(R)-3-amino-4-(2,4,5-trifluorophenyl)butanoyl]-3-(t-butoxymethyl)piperazin-2-one phosphate 501 mg of the compound obtained in Example 11 was dissolved in 3 mL of 2-propanol, to which 84 μl of a 85% phosphoric acid aqueous solution was then slowly added followed by stirring for 30 min. 3 mL of 2-propanol was added thereto, and the resulting mixture was stirred for 10 min and filtered to afford 100 mg of the title compound as a solid.

1H NMR (400 MHz, CD3OD): 7.33 (m, 1H), 7.19 (m, 1H), 4.81 (m, 1H), 4.58-4.41 (m, 1H), 3.94 (m, 1H), 3.85 (m, 2H), 3.65 (m, 1H), 3.37 (m, 2H), 3.22 (m, 1H), 2.95 (m, 2H), 2.69 (m, 2H), 1.17 (s, 3H), and 1.12 (s, 6H)

Mass (M+1): 402

Example 15

Preparation of (R)-4-[(R)-3-amino-4-(2,4,5-trifluorophenyl)butanoyl]-3-(t-butoxymethyl)piperazin-2-one acetate 500 mg of the compound obtained in Example 11 was dissolved in 3 mL of ethyl acetate to which a solution of 74.5 mg of acetic acid in 1 mL of ethyl acetate was then slowly added followed by stirring for 30 min. The reaction mixture was concentrated, to which 2 mL of ethyl acetate and 1 mL of 2-propanol were then added followed by stirring. 15 mL of hexane was added thereto, and the resulting mixture was stirred for 10 min and filtered to afford 495 mg of the title compound as a solid.

1H NMR (400 MHz, CD3OD): 7.32 (m, 1H), 7.20 (m, 1H), 4.79 (m, 1H), 4.60-4.40 (m, 1H), 3.94 (m, 1H), 3.87 (m, 2H), 3.70 (m, 1H), 3.34 (m, 2H), 3.24 (m, 1H), 2.90 (m, 2H), 2.76-2.58 (m, 2H), 1.94 (s, 3H), 1.17 (s, 3H), and 1.12 (s, 6H)

Mass (M+1): 402

Example 16

Preparation of (R)-4-[(R)-3-amino-4-(2,4,5-trifluorophenyl)butanoyl]-3-(t-butoxymethyl)piperazin-2-one malate 498 mg of the compound obtained in Example 11 was dissolved in 4 mL of acetone to which a solution of 166 mg of L-malic acid in 1 mL of acetone was then slowly added followed by stirring for 30 min. The reaction mixture was concentrated, to which 2 mL of ethyl acetate and 1 mL of 2-propanol were then added followed by stirring. 15 mL of hexane was added thereto, and the resulting mixture was stirred for 10 min and filtered to afford 506 mg of the title compound as a solid.

1H NMR (400 MHz, CD3OD): 7.34 (m, 1H), 7.21 (m, 1H), 4.80 (m, 1H), 4.58-4.39 (m, 1H), 4.26 (m, 1H), 3.94 (m, 1H), 3.84 (m, 2H), 3.71 (m, 1H), 3.36 (m, 2H), 3.22 (m, 1H), 3.02 (m, 2H), 2.82-2.63 (m, 3H), 2.50 (m, 1H), 1.17 (s, 3H), and 1.12 (s, 6H)

Mass (M+1): 402

Example 17

Preparation of (R)-4-[(R)-3-amino-4-(2,4,5-trifluorophenyl)butanoyl]-3-(t-butoxymethyl)piperazin-2-one succinate 498 mg of the compound obtained in Example 11 was dissolved in 3 mL of acetone to which a solution of 147 mg of succinic acid in 2 mL of acetone/water (20/1(v/v)) was then slowly added followed by stirring for 30 min. The reaction mixture was concentrated to dryness under reduced pressure to afford 596 mg of the title compound as a solid.

1H NMR (400 MHz, CD3OD): 7.34 (m, 1H), 7.21 (m, 1H), 4.81 (m, 1H), 4.58-4.40 (m, 1H), 3.95 (m, 1H), 3.85 (m, 2H), 3.70 (m, 1H), 3.36 (m, 2H), 3.25 (m, 1H), 2.92 (m, 2H), 2.81-2.64 (m, 2H), 2.51 (s, 4H), 1.18 (s, 3H), and 1.12 (s, 6H)

Mass (M+1): 402

Example 18

Preparation of (R)-4-[(R)-3-amino-4-(2,4,5-trifluorophenyl)butanoyl]-3-(t-butoxymethyl)piperazin-2-one adipate 503 mg of the compound obtained in Example 11 was dissolved in 4 mL of ethyl acetate to which a solution of 183 mg of adipic acid in 3 mL of acetone/water (30/1(v/v)) was then slowly added followed by stirring for 30 min. The reaction mixture was concentrated, to which 2 mL of ethyl acetate and 1 mL of 2-propanol were then added followed by stirring. 15 mL of hexane was added thereto, and resulting mixture was stirred for 10 min and filtered to afford 336 mg of the title compound as a solid.

1H NMR (400 MHz, CD3OD): 7.32 (m, 1H), 7.19 (m, 1H), 4.80 (m, 1H), 4.56-4.40 (m, 1H), 3.94 (m, 1H), 3.87 (m, 2H), 3.70 (m, 1H), 3.35 (m, 2H), 3.25 (m, 1H), 2.92 (m, 2H), 2.83-2.58 (m, 2H), 2.25 (m, 4H), 1.63 (m, 4H), 1.21 (s, 3H), and 1.12 (s, 6H)

Mass (M+1): 402

Experimental Example 1

DPP-IV Inhibitory Activity Assay

In order to examine DPP-IV inhibitory capacity of Inventive Compounds of Formula 1 prepared in Examples 1 through 18, the following experiments were carried out.

DPP-IV known as serine protease was purchased from R & D Systems. MK-0431 as control was prepared according to the method as disclosed in J. Med. Chem., 2005, 48, 141-151. In order to evaluate drug efficacy of Inventive Compounds of Formula 1, the binding activity of synthetic DPP-IV inhibitors was measured using the fluorogenic substrate Gly-Pro-AMC. The enzymatic reaction was carried out at 25° C. in a buffer solution containing 25 mM Tris/HCl (pH 8.0) by using 50 μM of Gly-Pro-AMC relative to 100 ng/mL of DPP-IV with varying concentrations of the inhibitor. $IC_{50}$, which is an inhibition constant of the inhibitor, was given by measuring the fluorescence with a spectrofluorometer after the enzymatic reaction for 1 hour, and then calculating a concentration of the inhibitor that is required to inhibit the enzymatic reaction of DPP-IV by 50%. The spectrofluorometer was a Tecan SpectraFluor spectrophotometer with an excitation wavelength of 360 nm and an emission wavelength of 465 nm. As a result, $IC_{50}$, measured as the capacity of the compound of Formula 1 to inhibit the activity of DPP-IV, was in the range of 0.5 to 20 nM (Table 1: in vitro human DPP-IV inhibitory activity). From this result, it can be seen that Inventive Compound of Formula 1 has very excellent DPP-IV inhibitory activity, as compared to the $IC_{50}$ value reported for commercially available JANUVIA or conventional DPP-IV inhibitor compounds (ranging from several hundreds of nM to several thousands of nM).

TABLE 1

| Example No. | $IC_{50}$ (nM) |
|---|---|
| MK-0431 | 28.3 |
| Example 1 | 0.72 |
| Example 2 | 7.4 |
| Example 3 | 2.2 |
| Example 4 | 4.3 |
| Example 5 | 1.7 |
| Example 6 | 11.0 |
| Example 7 | 17.4 |
| Example 8 | 5.2 |
| Example 9 | 1.3 |
| Example 10 | 48.7 |
| Example 11 | 0.8 |
| Example 12 | 1.05 |
| Example 13 | 0.81 |
| Example 14 | 0.92 |
| Example 15 | 0.87 |
| Example 16 | 0.73 |
| Example 17 | 1.2 |
| Example 18 | 0.71 |

Experimental Example 2

Oral Glucose Tolerance Test (OGTT)

In order to investigate anti-diabetic effects of a pharmaceutical composition comprising Inventive Compound of Formula 1 as an active ingredient, the oral glucose tolerance test (OGTT) was carried out which measures the body's ability to metabolize glucose within a given period of time.

For this purpose, laboratory animals (C57BL/6 mice) were fasted for 16 to 17 hours prior to the experiments. Blood was collected from caudal veins of animals in the morning on the day of the experiment and a blood glucose level was measured with an Accu-Chek Active Blood Glucose Meter (Roche Diagnostics). The pharmaceutical composition with a carrier was given orally 30 min prior to glucose administration (−30 min), followed by oral administration of a glucose solution (2 g/kg/10 mL) after 30 min (0 min). Blood collection was made at designated time points—just prior to drug administration, just prior to glucose administration, and 5, 15, 30, 60 and 90 min after glucose administration.

As a result, Examples 1, 3 and 12 exhibited superior blood glucose-lowering effects of 54%, 52% and 62%, respectively, at a dose of 1 mg/kg, as compared to the control group (no administration of a composition with a carrier). From these results, it can be seen that Inventive Compound of Formula 1 can be useful for the treatment of DPP-IV-related diseases including diabetes and obesity, because of high bioavailability.

Experimental Example 3

Pharmacokinetic/Pharmacodynamic Correlation of DPP-IV Inhibitor (Plasma DPP-IV Activity Vs. Drug Dose)

In order to ascertain anti-diabetic effects of Inventive Compound of Formula 1, comparative evaluation was made on the plasma DPP-IV inhibitory activity between Inventive Compounds and MK-0431. 8-week-old C57BL6 mice were orally administered with MK-0431 and Inventive Compound (compound of Example 1) at individual doses, followed by administration of glucose at a dose of 2 g/kg after 1 hour. 10 min later, blood was collected from eyes of animals. Blood plasma was obtained from the collected blood, and the plasma DPP-IV activity and plasma drug concentration were measured.

The plasma DPP-IV activity was given by measuring an amount of fluorescent AMC (7-Amino-4-methylcoumarin) liberated by the action of DPP-IV upon using Gly-Pro-AMC (Bachem, Switzerland) as a substrate. For this purpose, 50 μl of plasma was added to a reaction solution (100 mM HEPES, pH 7.6, 0.1 mg/mL, 50 μM Gly-Pro-AMC), and an AMC-release rate was calculated at 25° C. for 5 min.

Figure 1:
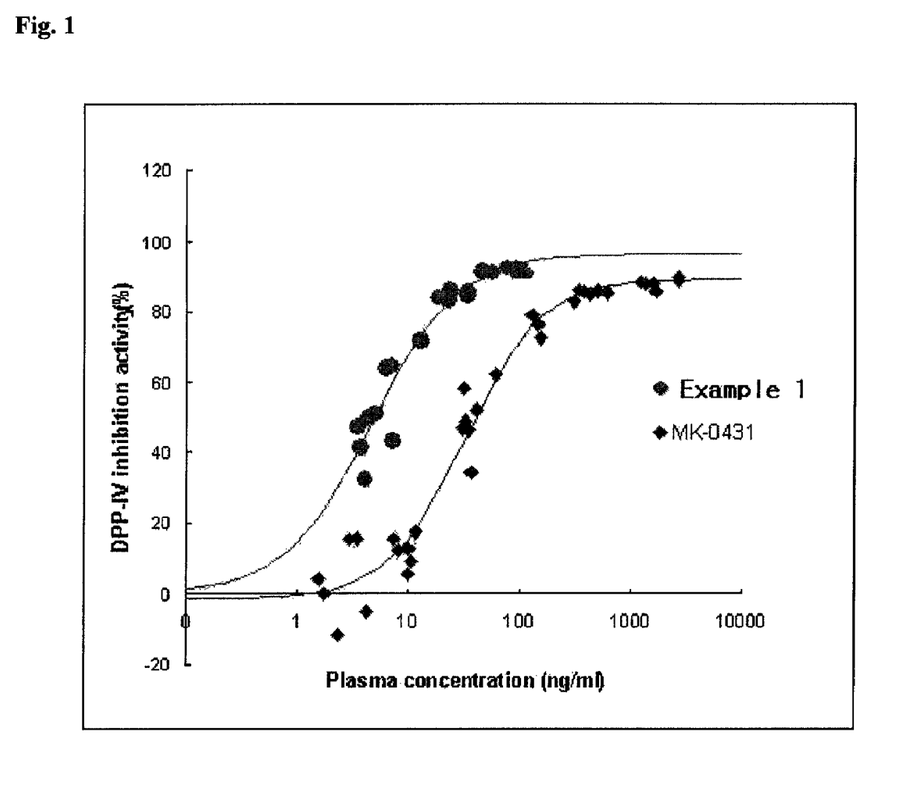
FIG. 1 shows correlations between plasma DPP-IV activity and drug dose, obtained for MK-0431 and a compound of Example 1.

As a result, the compound of Formula 1 (Example 1) exhibited 4 to 5-fold higher inhibitory activity at a plasma concentration of 10 ng/mL, in conjunction with 8 to 9-fold superior $EC_{50}$ (50% effective concentration) and $EC_{80}$ (80% effective concentration), when compared with MK-0431 (see FIG. 1).

Experimental Example 4

In Vivo DPP-IV Assay (Duration of DPP-IV Inhibitory Activity)

In order to investigate anti-diabetic effects of Inventive Compound of Formula 1, the plasma DPP-IV inhibitory activity and a duration thereof were comparatively evaluated between MK-0431 and Inventive Compound (Example 1), after administration of drug compounds in normal SD rats.

For this purpose, laboratory animals (SD rats) were fasted for 16 to 17 hours prior to the experiments. On the day of the experiment, the fasted animals were anesthetized with ether, followed by abdominal aortic cannulation. Thereafter, MK-0431 and Inventive Compound (Example 1) were diluted to 0.5% MC and administered to animals. Prior to drug administration (0h) and after designated periods of time following the drug administration, blood was collected in previously prepared 500 μl heparin tubes and the plasma was separated. 50 μl of plasma was added to each reaction solution (0.1 M HEPES, pH 7.6, 0.1 mg/mL, 50 μM Gly-Pro-AMC) and a kinetic study was carried out for 5 min to calculate a reaction rate.

Figure 2:
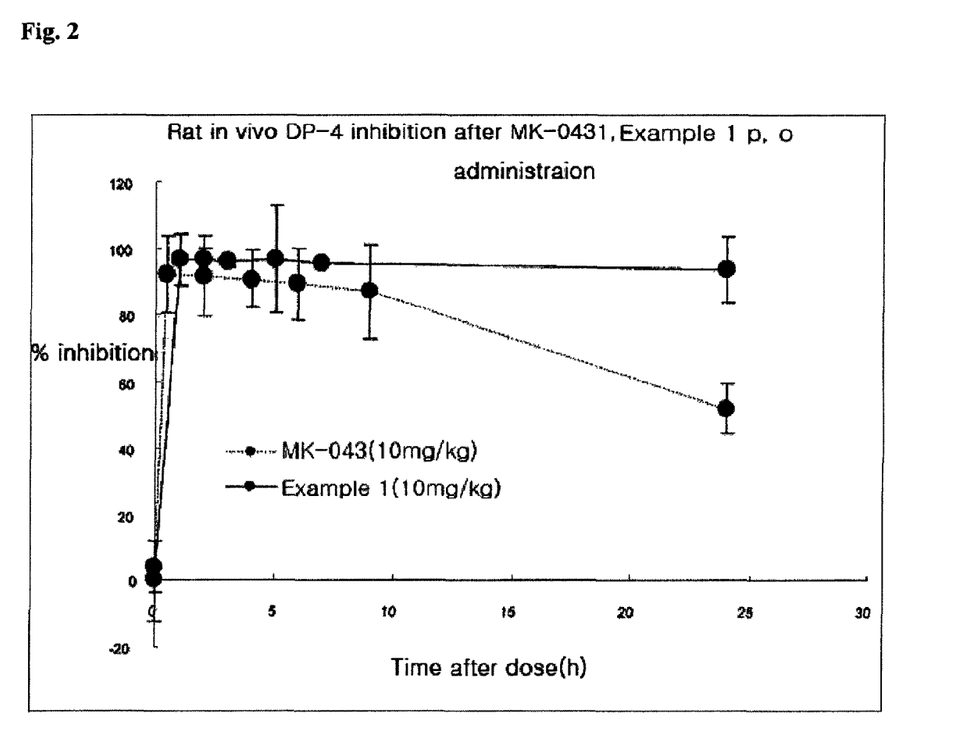
FIG. 2 shows measurement and comparison results of the duration of DPP-IV inhibitory activity obtained for MK-0431 and a compound of Example 1 in laboratory rats.

As a result, Inventive Compound at a dose of 10 mg/kg was found to retain 90% or more of DPP-IV inhibitory activity until 24 hours after administration, which is significantly higher activity, upon considering the fact that MK-0431 retained only about 50% of DPP-IV inhibitory activity after the same period of 24 hours (see FIG. 2).

Experimental Example 5

In Vivo Kinetic Experiments

In order to measure an in vivo half-life of Inventive Compound of Formula 1, normal SD rats (8-week old) were administered orally with MK-0431 and Inventive Compound (Examples 1, 3 and 12) at a dose of 10 mg/kg. Blood was sampled from the femoral aorta periodically and the in vivo retention time of the original compound was measured. As a result, Inventive Compound exhibited superior in vivo half-life (T1/2) to that of MK-0431.

TABLE 1

|  | Example 1 | Example 3 | Example 12 | MK-0431 |
| --- | --- | --- | --- | --- |
| T½ (hour) | 7.9 | 7.6 | 5.5 | 4.8 |

INDUSTRIAL APPLICABILITY

As apparent from the above description, the present invention enables production of a heterocyclic compound containing a beta-amino group, which has excellent inhibitory effects on activity of DPP-IV. Further, a pharmaceutical composition comprising the same compound of the present invention as an active ingredient exhibits excellent DPP-IV inhibitory activity and bioavailability and then can be useful for the prophylaxis or treatment of various diseases considered to be caused by DPP-IV, such as diabetes and obesity.

What is claimed is:
1. A compound represented by Formula 1:

(1)

wherein X is OR1, SR1 or NR1R2 wherein R1 and R2 are independently $C_1$ to $C_5$ lower alkyl, and R1 and R2 of NR1R2 may form a 5 to 7-membered ring with inclusion of a hetero atom O; or a stereoisomer or pharmaceutically acceptable salt thereof.

2. The compound of claim 1, wherein the compound is represented by Formula 2:

(2)

wherein X is as defined in claim 1; or a stereoisomer or pharmaceutically acceptable salt thereof.

3. The compound of claim 1, wherein the compound is selected from the group consisting of:
1) (R)-4-[(R)-3-amino-4-(2,4,5-trifluorophenyl)butanoyl]-3-(methoxymethyl)piperazin-2-one hydrochloride;
2) (R)-4-[(R)-3-amino-4-(2,4,5-trifluorophenyl)butanoyl]-3-(ethoxymethyl)piperazin-2-one hydrochloride;
3) (R)-4-[(R)-3-amino-4-(2,4,5-trifluorophenyl)butanoyl]-3-(isopropoxymethyl)piperazin-2-one hydrochloride;
4) (R)-4-[(R)-3-amino-4-(2,4,5-trifluorophenyl)butanoyl]-3-(t-butoxymethyl)piperazin-2-one hydrochloride;
5) (R)-4-[(R)-3-amino-4-(2,4,5-trifluorophenyl)butanoyl]-3-(cyclopentyloxymethyl)piperazin-2-one hydrochloride;
6) (R)-4-[(R)-3-amino-4-(2,4,5-trifluorophenyl)butanoyl]-3-[(diethylamino)methyl]piperazin-2-one dihydrochloride;
7) (R)-4-[(R)-3-amino-4-(2,4,5-trifluorophenyl)butanoyl]-3-[(ethylmethylamino) methyl]piperazin-2-one dihydrochloride;
8) (R)-4-[(R)-3-amino-4-(2,4,5-trifluorophenyl)butanoyl]-3-(morpholinomethyl)piperazin-2-one dihydrochloride;
9) (R)-4-[(R)-3-amino-4-(2,4,5-trifluorophenyl)butanoyl]-3-(t-butylthiomethyl)piperazin-2-one hydrochloride;
10) (S)-4-[(R)-3-amino-4-(2,4,5-trifluorophenyl)butanoyl]-3-(t-butoxymethyl)piperazin-2-one hydrochloride;
11) (R)-4-[(R)-3-amino-4-(2,4,5-trifluorophenyl)butanoyl]-3-(t-butoxymethyl)piperazin-2-one;
12) (R)-4-[(R)-3-amino-4-(2,4,5-trifluorophenyl)butanoyl]-3-(t-butoxymethyl)piperazin-2-one tartrate;
13) (R)-4-[(R)-3-amino-4-(2,4,5-trifluorophenyl)butanoyl]-3-(t-butoxymethyl)piperazin-2-one citrate;
14) (R)-4-[(R)-3-amino-4-(2,4,5-trifluorophenyl)butanoyl]-3-(t-butoxymethyl)piperazin-2-one phosphate;
15) (R)-4-[(R)-3-amino-4-(2,4,5-trifluorophenyl)butanoyl]-3-(t-butoxymethyl)piperazin-2-one acetate;
16) (R)-4-[(R)-3-amino-4-(2,4,5-trifluorophenyl)butanoyl]-3-(t-butoxymethyl)piperazin-2-one malate;
17) (R)-4-[(R)-3-amino-4-(2,4,5-trifluorophenyl)butanoyl]-3-(t-butoxymethyl)piperazin-2-one succinate; and 18) (R)-4-[(R)-3-amino-4-(2,4,5-trifluorophenyl)butanoyl]-3-(t-butoxymethyl)piperazin-2-one adipate.

4. A method for preparing a compound represented by Formula 2 of claim 2, comprising:
1) reacting a compound of Formula 3 having a beta amino group with a substituted heterocyclic compound of Formula 4 in the presence of 1-hydroxybenzotriazole (HOBT), 1-ethyl-3-(3-dimethylaminopropyl)carbodiimide (EDC) and tertiary amine to thereby prepare a compound of Formula 5, and
2) treating the compound of Formula 5 obtained from step (1) with an acid to prepare a compound of Formula 2:

wherein PG is a protecting group; and X is OR1, SR1 or NR1R2 wherein R1 and R2 are independently $C_1$ to $C_5$ lower alkyl, and R1 and R2 of NR1R2 may form a 5 to 7-membered ring with inclusion of a hetero atom O.

5. A pharmaceutical composition for the prevention and treatment of type 2 diabetes or obesity, comprising a compound of claim 1 represented by Formula 1 or a stereoisomer or pharmaceutically acceptable salt thereof as an active ingredient.

6. The composition of claim 5, wherein the compound is selected from the group consisting of:
1) (R)-4-[(R)-3-amino-4-(2,4,5-trifluorophenyl)butanoyl]-3-(t-butoxymethyl)piperazin-2-one hydrochloride;
2) (R)-4-[(R)-3-amino-4-(2,4,5-trifluorophenyl)butanoyl]-3-(ethoxymethyl)piperazin-2-one hydrochloride;
3) (R)-4-[(R)-3-amino-4-(2,4,5-trifluorophenyl)butanoyl]-3-(isopropoxymethyl)piperazin-2-one hydrochloride;
4) (R)-4-[(R)-3-amino-4-(2,4,5-trifluorophenyl)butanoyl]-3-(methoxymethyl)piperazin-2-one hydrochloride;
5) (R)-4-[(R)-3-amino-4-(2,4,5-trifluorophenyl)butanoyl]-3-(cyclopentyloxymethyl)piperazin-2-one hydrochloride;
6) (R)-4-[(R)-3-amino-4-(2,4,5-trifluorophenyl)butanoyl]-3-[(diethylamino)methyl]piperazin-2-one dihydrochloride;
7) (R)-4-[(R)-3-amino-4-(2,4,5-trifluorophenyl)butanoyl]-3-[(ethylmethylamino)methyl]piperazin-2-one dihydrochloride;
8) (R)-4-[(R)-3-amino-4-(2,4,5-trifluorophenyl)butanoyl]-3-(morpholinomethyl)piperazin-2-one dihydrochloride;
9) (R)-4-[(R)-3-amino-4-(2,4,5-trifluorophenyl)butanoyl]-3-(t-butylthiomethyl)piperazin-2-one hydrochloride;
10) (S)-4-[(R)-3-amino-4-(2,4,5-trifluorophenyl)butanoyl]-3-(t-butoxymethyl)piperazin-2-one hydrochloride;
11) (R)-4-[(R)-3-amino-4-(2,4,5-trifluorophenyl)butanoyl]-3-(t-butoxymethyl)piperazin-2-one;
12) (R)-4-[(R)-3-amino-4-(2,4,5-trifluorophenyl)butanoyl]-3-(t-butoxymethyl)piperazin-2-one tartrate;
13) (R)-4-[(R)-3-amino-4-(2,4,5-trifluorophenyl)butanoyl]-3-(t-butoxymethyl)piperazin-2-one citrate;
14) (R)-4-[(R)-3-amino-4-(2,4,5-trifluorophenyl)butanoyl]-3-(t-butoxymethyl)piperazin-2-one phosphate;
15) (R)-4-[(R)-3-amino-4-(2,4,5-trifluorophenyl)butanoyl]-3-(t-butoxymethyl)piperazin-2-one acetate;
16) (R)-4-[(R)-3-amino-4-(2,4,5-trifluorophenyl)butanoyl]-3-(t-butoxymethyl)piperazin-2-one malate;
17) (R)-4-[(R)-3-amino-4-(2,4,5-trifluorophenyl)butanoyl]-3-(t-butoxymethyl)piperazin-2-one succinate; and
18) (R)-4-[(R)-3-amino-4-(2,4,5-trifluorophenyl)butanoyl]-3-(t-butoxymethyl)piperazin-2-one adipate.

7. A method for treating type 2 diabetes or obesity, comprising administering an effective amount of a composition comprising the compound of claim 1 to a mammal in need thereof.

8. The method of claim 4, wherein PG is Boc.

9. A compound represented by Formula 4:

wherein X is OR1, SR1 or NR1R2 wherein R1 and R2 are independently $C_1$ to $C_5$ lower alkyl, and R1 and R2 of NR1R2 may form a 5 to 7-membered ring with inclusion of a hetero atom O.

10. The compound of claim 9, wherein the X is selected from the group consisting of tert-butoxy, methoxy, ethoxy, isopropoxy, cyclopentyloxy, diethylamino, ethylmethylamino, morpholino and tert-butylthio.

11. The compound of claim 9, wherein the X is tert-butoxy.

12. A method for treating type 2 diabetes or obesity, comprising administering an effective amount of a composition comprising the compound of claim 2 to a mammal in need thereof.

13. A method for treating type 2 diabetes or obesity, comprising administering an effective amount of a composition comprising the compound of claim 3 to a mammal in need thereof.

* * * * *